US009753042B2

(12) United States Patent
Beaman

(10) Patent No.: US 9,753,042 B2
(45) Date of Patent: Sep. 5, 2017

(54) KITS FOR DETERMINING MALE FERTILITY BY MEASURING LEVELS OF A2V-ATPASE, G-CSF, MIP 1 ALPHA, MCP-1, AND METHODS AND KITS FOR IMPROVING REPRODUCTIVE OUTCOMES IN ARTIFICIAL INSEMINATION PROCEDURES

(71) Applicant: Rosalind Franklin University of Medicine and Science, North Chicago, IL (US)

(72) Inventor: Kenneth Beaman, Gurnee, IL (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 0 days.

(21) Appl. No.: 14/258,674

(22) Filed: Apr. 22, 2014

(65) Prior Publication Data
US 2014/0315761 A1 Oct. 23, 2014

Related U.S. Application Data

(60) Provisional application No. 61/815,199, filed on Apr. 23, 2013.

(51) Int. Cl.
*G01N 33/68* (2006.01)
(52) U.S. Cl.
CPC .................. *G01N 33/689* (2013.01)
(58) Field of Classification Search
CPC .... G01N 33/689; G01N 33/53; G01N 33/543; G01N 33/54313; Y10S 436/808; Y10S 436/814
See application file for complete search history.

(56) References Cited

U.S. PATENT DOCUMENTS

| 5,981,180 A * | 11/1999 | Chandler | G01N 15/1012 435/6.12 |
|---|---|---|---|
| 2004/0058385 A1 | 3/2004 | Abel et al. | |
| 2004/0241776 A1* | 12/2004 | Geister | G01N 33/54306 435/7.92 |
| 2004/0259865 A1* | 12/2004 | Harada | C07D 239/34 514/227.5 |
| 2005/0191687 A1 | 9/2005 | Wang et al. | |
| 2006/0019256 A1* | 1/2006 | Clarke | C12N 5/0695 435/6.14 |
| 2007/0099248 A1 | 5/2007 | Ting et al. | |
| 2009/0272913 A1 | 11/2009 | Naciri et al. | |
| 2013/0065249 A1 | 3/2013 | Tan et al. | |

FOREIGN PATENT DOCUMENTS

| JP | 2008528973 A | 7/2008 |
|---|---|---|
| JP | 2009544934 A | 12/2009 |
| WO | 03094847 A2 | 11/2003 |
| WO | 2005005601 A2 | 1/2005 |
| WO | 2012129610 A1 | 10/2012 |

OTHER PUBLICATIONS

Morse., Critical factors in an enzyme immunoassay (ELISA) for antibodies to mouse thymic virus (MTLV), Laboratory Animals, 1990, 24, pp. 313-320.*
Baker et al., Conversion of a Capture ELISA to a Luminex xMAP Assay using a Multiplex Antibody Screening Method, Journal of visualized Experiments, Jul. 2012, 65, pp. 1-8.*
International Search Report for PCT/US2014/035122 mailed Oct. 7, 2014 (3 pages).
Written Opinion of International Searching Authority for PCT/US2014/035122 mailed Oct. 7, 2014 (6 pages).
Brahmaraju et al. "Spatio-temporal organization of Vam6P and SNAP on mouse spermatozoa and their involvement in sperm-zona pellucida interactions," Biochemical and Biophysical Research Communications, May 21, 2004 (May 21, 2004), vol. 318, pp. 148-155.
Ota et al. "Expression of a2 Vacuolar ATPase in Spermatozoa is Associated with Semen Quality and Chemokine-Cytokine Profiles in Infertile Men," PLoS ONE, Jul. 30, 2013 (Jul. 30, 2013), vol. 8, e70470, pp. 1-7.
Japanese Patent Office, Office Action in Japanese Application No. 2016-507912 mailed Aug. 9, 2016 (8 pages including translation).
Jaiswal, M., et al.; "V-ATPase upregulation during early pregnancy: a possible link to establishment of an inflammatory response during preimplantation period of pregnancy"; Society of Reproduction and Fertility; 143: 713-725 (2012); ISSN 1470-1626 (paper) 1741-7899 (online) (13 pages).
Merkulova, M., et al.; "N-terminal domain of the V-ATPase a2-subunit displays integral membrane protein properties"; Protein Sci.; Oct. 2010; 19(10): 1850-1862; published online Jul. 28, 2010 (14 pages).
Luminex Corporation; Product Information Sheet for "MagPlex Microspheres"; 89-60000-00-049 Rev K; Feb. 2014 (2 pages), Feb. 2014.
Luminex Corporation; Product Information Sheet for "MicroPlex Microspheres (LC10001 thru LC10500)"; 89-60000-00-068 Rev B; Mar. 2010 (2 pages), Mar. 2010.
Futai M, Oka T, Sun-Wada G, Moriyama Y, Kanazawa H, Wada Y. "Luminal acidification of diverse organelles by V-ATPase in animal cells." J Exp Biol 2000;203:107-16.

(Continued)

*Primary Examiner* — Gary W Counts
(74) *Attorney, Agent, or Firm* — Joseph A. Fuchs; Greensfelder, Hemker & Gale, P.C.

(57) ABSTRACT

The present invention provides a kit for determining male fertility including a container system containing a plurality of enzyme-linked antibodies one of each capable of binding to analytes Atp6v0a2, G-CSF, MIP 1α, and MCP-1. The kit further includes suitable packaging and a set of instructions for using the enzyme-linked antibodies with a seminal sample to determine the fertility of the sample.

14 Claims, 3 Drawing Sheets

(56) References Cited

OTHER PUBLICATIONS

Nelson N, Harvey WR. "Vacuolar and plasma membrane proton-adenosinetriphosphatases." Physiol Rev 1999;79:361-85.
Wagner CA, et al.; "Renal vacuolar H+-ATPase"; Physiol Rev 2004;84:1263-314.
Toyomura T, et al.; "From lysosomes to the plasma membrane: localization of vacuolar-type H+-ATPase with the a3 isoform during osteoclast differentiation"; J Biol Chem 2003;278:22023-30.
Pietrement C, et al.; "Distinct expression patterns of different subunit isoforms of the V-ATPase in the rate epididymis"; Biol Reprod 2006;74:185-94.
Sun-Wada GH, et al.; "A proton pump ATPase with testis-specific E1-subunit isoform required for acrosome acidification"; J Biol Chem 2002;277:18098-105.
Jaiswal MK, et al.; "V-ATPase upregulation during early pregnancy: a possible link to establishment of an inflammatory response preimplantation period of pregnancy"; Reproduction 2012;143:713-25.
Robertson SA; "Seminal plasma and male factor signalling in the female reproductive tract"; Cell Tissue Res 2005;322:43-52.
Kelly RW. "Prostaglandins in primate semen: biasing the immune system to benefit spermatozoa and virus?"; Prostaglandins Leukot Essent Fatty Acids 1997;57:113-8.
Sharkey DJ, et al.; "Seminal plasma differentially regulates inflammatory cytokine gene expression in human cervical and vaginal epithelial cells"; Mol Hum Reprod 2007;13:491-501.
Kauma SW. "Cytokines in implantation"; J Reprod Fertil Suppl 2000;55:31-42.
Romero R, et al.; "Human decidua: a source of interleukin-1"; Obstet Gynecol 1989;73:31-4.
Brisseau GF, et al.; "Interleukin-1 increases vacuolar-type H+-ATPase activity in murine peritoneal macrophages"; J Biol Chem 1996;271:2005-11.
Ntrivalas E, et al.; "The N-terminus domain of the a2 isoform of vacuolar ATPase can regulate interleukin-1beta production from mononuclear cells in co-culture with JEG-3 choriocarcinoma cells"; Am J Reprod Immunol 2007;57:201-9.
Kwong C, et al.; "Tumor-associated a2 vacuolar ATPase acts as a key mediator of cancer-related inflammation by inducing pro-tumorigenic properties in monocytes"; J Immunol 2011;186:1781-9.
Kolettis PN. "Evaluation of the subfertile man"; Am Fam Physician, 2003;67:2165-72.
Guzick DS, et al.; "Sperm morphology, motility, and concentration in fertile and infertile men"; N Engl J Med 2001;345:1388-93.
Andersen AN, et al.; "Assisted reproductive technology in Europe, 2001. Results generated from European registers by ESHRE" Hum Reprod 2005;20:1158-76.
Kruger TF, et al.; "Predictive value of abnormal sperm morphology in in vitro fertilization"; Fertil Steril 1988;49:112-7.
Cooper TG, et al.; "World Health Organization reference values for human semen characteristics." Hum Reprod Update 2010;16:231-45.
Ainsworth C. "Cell biology: the secret life of sperm." Nature 2005;436:770-1.
Ostermeier GC, et al.; "Reproductive biology; delivering spermatozoan RNA to the oocyte." Nature 2004;429:154.
Ostermeier GC, et al.; "Spermatozoal RNA profiles of normal fertile men." Lancet 2002;360:772-7.
Acott TS, Carr DW. "Inhibition of bovine spermatozoa by caudal epididymal fluid: II. Interaction of pH and a quiescence factor." Biol Reprod 1984;30:926-35.
Carr DW, Acott TS. "Inhibition of bovine spermatozoa by caudal epididymal fluid: I. Studies of a sperm motility quiescence factor." Biol Reprod 1984;30:913-25.
Acott TS, Samples JR, Bradley JM, Bacon DR, Bylsma SS, Van Buskirk EM. "Trabecular repopulation by anterior trabecular meshwork cells after laser trabeculoplasty." Am J Ophthalmol 1989;107:1-6.

Hamamah S, Gatti JL. "Role of the ionic environment and internal pH on sperm activity." Hum Reprod 1998;13 Suppl 4:20-30.
Lishko PV, Botchkina IL, Fedorenko A, Kirichok Y. "Acid extrusion from human spermatozoa is mediated by flagellar voltage-gated proton channel." Cell 2010;140:327-37.
Marshansky V. "The V-ATPase a2-subunit as a putative endosomal pH-sensor." Biochem Soc Trans 2007;35:1092-9.
Chaouat G, Dubanchet S, Ledee N. "Cytokines: Important for implantation?" J Assist Reprod Genet 2007;24:491-505.
Chaouat G, Petitbarat M, Dubanchet S, Rahmati M, Ledee N. "Tolerance to the foetal allograft?" Am J Reprod Immunol 2010;63:624-36.
Mor G, Cardenas I, Abrahams V, Guller S. "Inflammation and pregnancy: the role of the immune system at the implantation site." Ann N Y Acad Sci 2011;1221:80-7.
Rossi D, Zlotnik A. "The biology of chemokines and their receptors." Annu Rev Immunol 2000;18:217-42.
Garcia-Velasco JA, Arici A. "Chemokines and human reproduction." Fertil Steril 1999;71:983-93.
Carr MW, Roth SJ, Luther E, Rose SS, Springer TA. "Monocyte chemoattractant protein 1 acts as a T-lymphocyte chemoattractant." Proc Natl Acad Sci U S A 1994;91:3652-6.
Xu LL, Warren MK, Rose WL, Gong W, Wang JM. "Human recombinant monocyte chemotactic protein and other C—C chemokines bind and induce directional migration of dendritic cells in vitro." J Leukoc Biol 1996;60:365-71.
Gu L, Tseng S, Horner RM, Tam C, Loda M, Rollins BJ. "Control of TH2 polarization by the chemokine monocyte chemoattractant protein-1." Nature 2000;404:407-11.
He YY, He XJ, Guo PF, Du MR, Shao J, Li MQ et al. "The decidual stromal cells-secreted CCL2 induces and maintains decidual leukocytes into Th2 bias in human early pregnancy." Clin Immunol 2012;145:161-73.
Sharkey DJ, Tremellen KP, Jasper MJ, Gemzell-Danielsson K, Robertson SA. "Seminal fluid induces leukocyte recruitment and cytokine and chemokine mRNA expression in the human cervix after coitus." J Immunol 2012;188:2445-54.
Arici A, Senturk LM, Seli E, Bahtiyar MO, Kim G. "Regulation of monocyte chemotactic protein-1 expression in human endometrial stromal cells by estrogen and progesterone." Biol Reprod 1999;61:85-90.
Jones RL, Kelly RW, Critchley HO. "Chemokine and cyclooxygenase-2 expression in human endometrium coincides with leukocyte accumulation." Hum Reprod 1997;12:1300-6.
Pollard JW, Lin EY, Zhu L. "Complexity in uterine macrophage responses to cytokines in mice." Biol Reprod 1998;58:1469-75.
Wood GW, et al.; "Relative role of CSF-1, MCP-1/JE, and RANTES in macrophage recruitment during successful pregnancy." Mol Reprod Dev 1997;46:62-9; discussion 9-70.
Xie ZF, et al.; "Effects of antigen presentation of eosinophils on lung Th1 /Th2 imbalance." Chin Med J (Engl) 2005;118:6-11.
Strath M, Sanderson CJ. "Production and functional properties of eosinophils from bone marrow cultures." J Cell Sci 1985;74:207-17, Oct. 14, 2016.
Sugita K, et al.; "Granulocyte colony stimulation factor (G-CSF) suppresses interleukin (IL)-12 and/or IL-2 induced interferon (IFN)-gamma production and cytotoxicity of decidual mononuclear cells." Am J Reprod Immunol 2003;50:83-9.
Niessen H, et al.; "Granulocyte colony-stimulating factor upregulates the vacuolar proton ATPase in human neutrophils." Blood 1997;90:4598-601.
Robertson SA. "GM-CSF regulation of embryo development and pregnancy." Cytokine Growth Factor Rev 2007;18:287-98.
De Jonge C. "Semen analysis: looking for an upgrade in class." Fertil Steril 2012;97:260-6.
Lamb DJ. "Semen analysis in 21st century medicine: the need for sperm function testing." Asian J Androl 2010;12:64-70.
Handelsman DJ, Cooper TG. "Foreword to Semen Analysis in 21st Century Medicine special issue in Asian Journal of Andrology." Asian J Androl 2010;12:7-10.
Naz RK, Kaplan P. "Interleukin-6 enhances the fertilizing capacity of human sperm by increasing capacitation and acrosome reaction." J Androl 1994;15:228-33.

(56) References Cited

OTHER PUBLICATIONS

Naz RK, Kaplan P. "Increased levels of interleukin-6 in seminal plasma of infertile men." J Androl 1994;15:220-7.
Gruschwitz MS, Brezinschek R, Brezinschek HP. "Cytokine levels in the seminal plasma of infertile males." J Androl 1996;17:158-63.
Paradisi R, et al.; "T-helper 2 type cytokine and soluble interleukin-2 receptor levels in seminal plasma of infertile men." Am J Reprod Immunol 1997;38:94-9.
Eggert-Kruse W, et al.; "Relationship of seminal plasma interleukin (IL)-8 and IL-6 with semen quality." Hum Reprod 2001;16:517-28.
Sanocka D, et al.; "Male genital tract inflammation: The role of selected interleukins in regulation of pro-oxidant and antioxidant enzymatic substances in seminal plasma." J Androl 2003;24:448-55.
Bezold G, et al.; "Prevalence of sexually transmissible pathogens in semen from asymptomatic male infertility patients with and without leukocytospermia." Fertil Steril 2007;87:1087-97.
Dousset B, et al.; "Seminal cytokine concentrations (IL-1beta, IL-2, IL-6, sR IL-2, sR IL-6), semen parameters and blood hormonal status in male infertility." Hum Reprod 1997;12:1476-9.
Camejo MI, Segnini A, Proverbio F. "Interleukin-6 (IL-6) in seminal plasma of infertile men, and lipid peroxidation of their sperm." Arch Androl 2001;47:97-101.
Matalliotakis I, et al.; "Distinct expression pattern of cytokines in semen of men with genital infection and oligo-terato-asthenozoospermia." Am J Reprod Immunol 2002;48:170-5.
Hedger MP, Meinhardt A. "Cytokines and the immune-testicular axis." J Reprod Immunol 2003;58:1-26.

\* cited by examiner

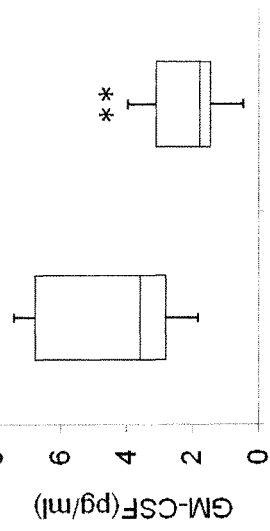
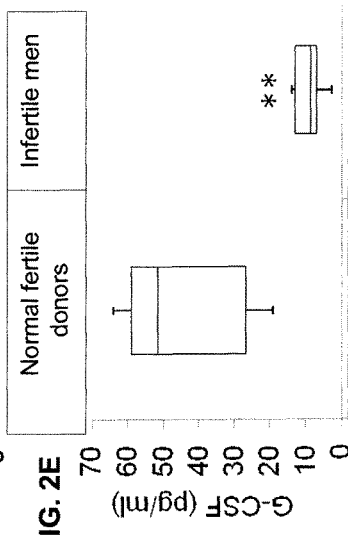
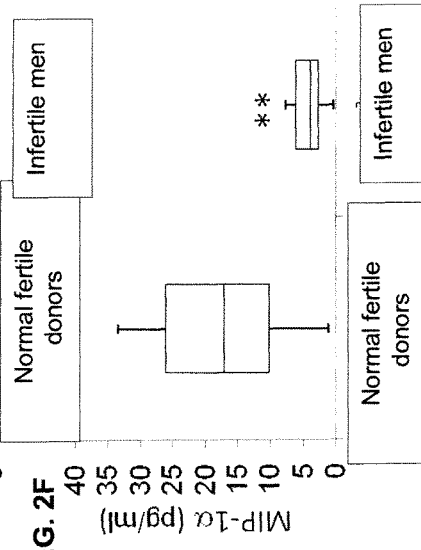
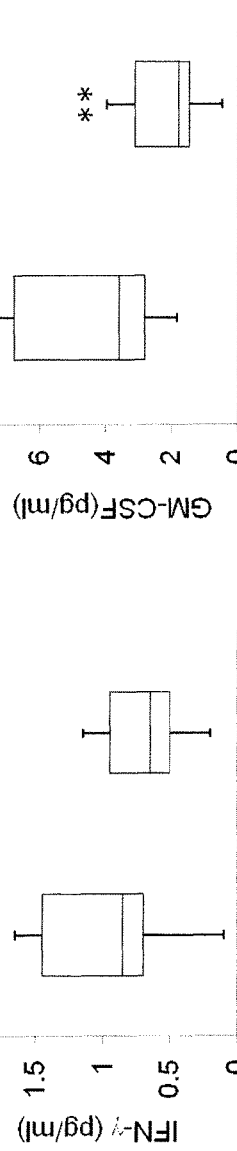
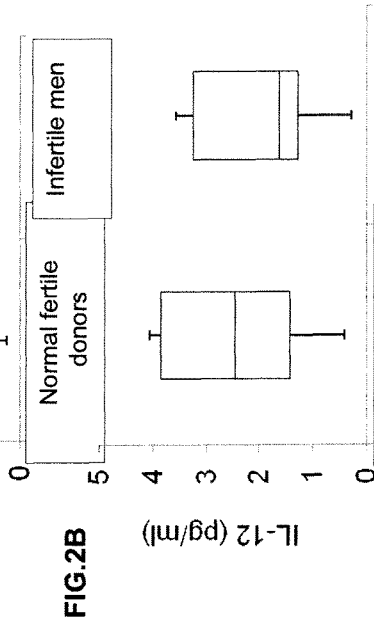
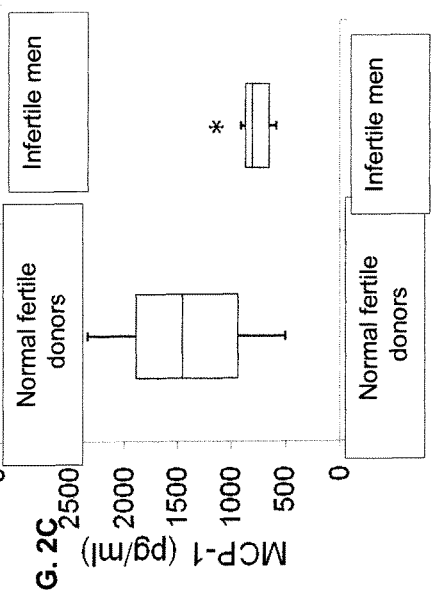

KITS FOR DETERMINING MALE FERTILITY BY MEASURING LEVELS OF A2V-ATPASE, G-CSF, MIP 1 ALPHA, MCP-1, AND METHODS AND KITS FOR IMPROVING REPRODUCTIVE OUTCOMES IN ARTIFICIAL INSEMINATION PROCEDURES

CROSS-REFERENCE TO RELATED APPLICATIONS

This application claims priority to U.S. Provisional Patent Application Ser. No. 61/815,199 filed on Apr. 23, 2013 which is incorporated in its entirety by reference herein and is made a part of.

SEQUENCE LISTING

The instant application contains a Sequence Listing which has been submitted electronically in ASCII format and is hereby incorporated by reference in its entirety. Said ASCII copy, created on Oct. 2, 2015, is named 295792-007121_SL.txt and is 739 bytes in size.

BACKGROUND OF THE INVENTION

Field of the Invention

The present invention relates generally to determining male fertility by measuring the quantity of specific analytes in samples of seminal fluid and more specifically to kits for detecting the concentration of a2V-ATPase, G-CSF, MIP 1α, MCP-1 in such samples.

Background of the Invention

The vacuolar (H+)-ATPase (V-ATPase) is a multi subunit enzyme that couples ATP hydrolysis to the pumping of protons across plasma membranes. It is ubiquitously expressed in eukaryotic cells, where it participates in the acidification of highly differentiated organelles, including the Golgi apparatus, lysosomes, endosomes, and secretory vesicles. In addition, the V-ATPase is also found at high density in the plasma membrane of specialized epithelial cells that are involved in active proton transport and pH regulation of extracellular compartments. Those plasma membrane V-ATPases have important roles in such processes as renal acidification, bone resorption or sperm capacitation. In a murine study, V-ATPases in the apical membrane of epididymal clear cells, which are also controlled by reversible endocytosis and exocytosis, are required for sperm maturation, viability and pH homeostasis. In addition, the a2 isoform of V-ATPase (Atp6v0a2) is located specifically in the acrosomal membrane of murine sperm to regulate an acidic intra-acrosomal pH, which is necessary for processing protease zymogen, essential for fertilization. In agreement with this previous study, Atp6v0a2 was highly expressed in the acrosomal region of the capacitated murine sperm but not detected in non-capacitated sperm from the caudal epididymis. This study provided a new insight into a possible association with Atp6v0a2 and fertilizing ability of capacitated human sperm, since capacitation is required for fertilization and embryogenesis.

Although seminal fluid has been conventionally viewed as transport media for spermatozoa traversing the female reproductive tissues, it is now known to have broader biological actions in regulating female fertility. Seminal fluid contains a complex array of cytokines, chemokines, and other bioactive molecules. Seminal fluid induces pro-inflammatory cytokines and chemokines such as GM-CSF, IL-6, IL-8, MCP-1, MIP-3α, and IL-1α in the female reproductive tract. Particularly, IL-1 has a potential role in the regulation of blastocyst implantation during early pregnancy. IL-1 enhances V-ATPase activity, and increased level of IL-1 may feed back to down regulate the innate immune response, which is essential for implantation. We have shown that Atp6v0a2 can regulate IL-1β as well as IL-1α with little or no subsequent increase in TNF-α secretion. In addition, capacitation appears to cause the release of a2NTD, which is the N-terminal portion from Atp6v0a2. We have shown that a2NTD induces maternal inflammatory cytokines such as LIF, IL-1β, TNF-α and MIP-1α, and exposure of the uterus to sperm accompanied by seminal fluid enhances pregnancy success rate. Therefore, Atp6v0a2 derived from capacitated sperm may play a key role in expression of cytokines and chemokines in the uterus and placenta and controls early inflammatory process which is necessary for implantation and placentation.

In approximately 30% of couples, male factor infertility is the only cause of infertility, and in another 20% to 30% of couples, it is a contributing factor for their infertility. Semen analysis is the most commonly used diagnostic tool for male infertility. Recently, the World Health Organization (WHO) has issued standards for abnormal semen analysis in 2010 (Cooper). However, these standards are not quantitative and do not identify abnormal parameters related to the underlying causes of infertility. To issue these standards semen obtained only from fertile men were used, and there were no "threshold values" for sperm concentration, motility, and morphology to differentiate men as subfertile, of indeterminate fertility, or fertile. Thus, none of these parameters can predict the fertile capacity of sperm or pregnancy outcome with a great deal of confidence. Unfortunately, most clinical laboratories still rely on semen analysis only based on standards to determine plan of care. Indeed, even with techniques such as IVF or IVF with intracytoplasmic sperm injection (ICSI), pregnancy success rates are still remain at 25-30%. This could be partly related to lack of our understanding of the molecular pathology of sperm and semen. Therefore, if a new biomarker could be associated with sperm from infertile men, this would provide a better method to predict fertilization capacity of sperm and pregnancy outcome.

Based on the findings from our lab and others, we hypothesize that Atp6v0a2 in human sperm contributes to the establishment of "immunological privilege". In this study, we investigated Atp6v0a2 expression and localization in human sperm, and examined the possibility of Atp6v0a2 as a useful biomarker for male factor infertility.

These and other aspects and attributes of the present invention will be discussed with reference to the following drawings and accompanying specification.

SUMMARY OF THE INVENTION

The present invention provides a kit for determining male fertility having a first container system containing a plurality of enzyme-linked antibodies one of each for Atp6v0a2, G-CSF, MIP 1α, and MCP-1; packaging for holding the first container system; and instructions for using the enzyme-linked antibodies with a seminal sample to determine the fertility of the sample.

The present invention further provides a method for determining the fertility of a semen sample by determining the quantities of Atp6v0a2, G-CSF, MIP 1α, and MCP-1 and comparing to the quantities of these proteins in a control sample.

The present invention further provides a method of preparing sperm and seminal plasma samples for artificial insemination to increase the fertilization outcome.

BRIEF DESCRIPTION OF THE DRAWINGS

FIG. 1A. Atp6v0a2 mRNA expression in spermatozoa was analyzed by RT-PCR. All data were normalized to β-actin mRNA. Atp6v0a2 mRNA expression in spermatozoa of normal fertile donors was significantly higher than that of infertile men (P=0.027, n=18 each); FIG. 1B. Western blots indicate strong expression of Atp6v0a2 in spermatozoa of normal fertile donors but weak in spermatozoa of infertile men. Western blot figure was a representative sample. β-actin served as a loading control. Histogram shows quantification of Atp6v0a2 protein expression, as determined by densitometry and normalized to β-actin. Atp6v0a2 protein expression of spermatozoa was significantly higher in normal fertile donors as compared to infertile men (P<0.05, n=5 each). FIG. 1C. The a2NTD was quantified by ELISA. Seminal fluid a2NTD of normal fertile donors was significantly higher than that of infertile men (P≤0.01, n=20 each). FIG. 1D. Western blot analysis detected strong expression of a2NTD in seminal fluid of normal fertile donors at 20 kDa band, but not in infertile men. β-actin served as a loading control. Histogram shows relative quantification of a2NTD peptide by densitometric evaluation relative to β-actin. Seminal fluid a2NTD level was significantly higher in normal fertile donors than infertile men (P≤0.05, n=6). (*P<0.05; **P<0.01 with respect to normal fertile donors)

FIGS. 2A-2F: The concentration of cytokines and chemokines in seminal fluid from infertile men and normal fertile donors (n=20 each) measured by Luminex assay. A,B; IFN-γ and IL-12 were not significantly different between normal fertile donors and infertile men. C-F; MCP-1 (P≤0.05), GM-CSF (P≤0.01), G-CSF (P≤0.01) and MIP-1α (P≤0.01) in infertile men were significantly decreased compared to normal fertile donors. (*P<0.05; **P<0.01 with respect to normal fertile donors)

FIG. 3A. Western blot analysis of Atp6v0a2 in human motile and immotile spermatozoa using antibody to Atp6v0a2 (2C1), revealed a single protein band at 100 kDa. FIG. 3B. Histogram showed quantification of Atp6v0a2 protein expression, as determined by densitometry and normalized to β-actin. Immotile spermatozoa had significantly lower Atp6v0a2 expression than motile spermatozoa (P≤0.01, n=6). (*P<0.01 with respect to normal fertile donors)

FIG. 3C. Immunofluorescent microscopy of immotile and motile spermatozoa stained with anti-Atp6v0a2-FITC (green) and DAPI (blue for nuclear stain) to demonstrate location of this protein. Panel 1. indicates no expression occurs in immotile spermatozoa. Panel 2. indicates high expression of Atp6v0a2 in the acrosomal region of motile spermatozoa. Data are representative of five experiments.

DETAILED DESCRIPTION OF THE INVENTION

Figure 1A:
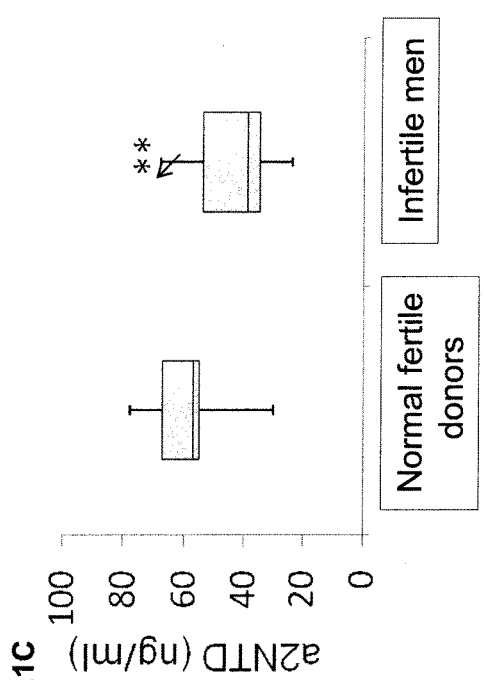
FIGS. 1A-1D: Atp6v0a2 mRNA and protein expression in spermatozoa and seminal fluid was studied in normal fertile donors and infertile men.

While this invention is susceptible of embodiments in many different forms, there are specific embodiments which will be described herein in detail with the understanding that the present disclosure is to be considered as an exemplification of the principles of the invention and is not intended to limit the invention to the specific embodiments illustrated.

Semen Analysis

Semen samples were obtained from 35 consecutive men who were diagnosed with male infertility and were undergoing assisted reproduction techniques (ART) such as IVF/ICSI at the Andrology Lab, Chicago, Ill. Duration of infertility was at least 12 months or more, and azospermic men were excluded from the study. Additionally, semen samples were obtained from 35 fertile donors before they had vasectomy for male sterilization. The study was approved by the IRB of the Rosalind Franklin University of Medicine and Science. Informed consent was obtained from all study patients and controls prior to enter the study, which was approved by the local Institutional Review Board (IRB).

Before the implementation of the ART, semen samples were collected in sterile containers by masturbation after 3-5 days of sexual abstinence. After liquefaction of the semen at room temperature (22° C.) for 30 minutes, the samples were assessed for ejaculate volume (ml), sperm concentration ($n \times 10^6$/mL), motility (%), and morphology (normal forms, %). Sperm morphology was studied using Kruger's strict criteria. The samples were classified according to 2010 WHO semen analysis guidelines (normal sperm: ≥15/million/mL, ≥32% progressive motility, and ≥4% normal forms). All the sperm samples were evaluated by one of two fellowship-trained clinical andrologists. An aliquot of each semen sample was collected by centrifugation at 400×g for 10 minutes to obtain sperm-free seminal plasma and then frozen at −80° C. until analysis was made.

Isolation of Motile and Immotile Sperm from Semen by Density Centrifugation

PureSperm gradients 40% and 80% (Nidacon, Gothenburg, Sweden) were used for the experiments. Media were warmed to 37° C. temperature before use. Using a sterile pipette 2.0 mL of the "lower layer" (80% PureSperm gradient) was transferred into a conical centrifuge tube. Using a new sterile pipette 2.0 mL of the "upper layer" (40% PureSperm gradient) was gently dispensed on top of the lower layer. A liquefied semen sample was then placed on top of the upper layer and the tube was centrifuged for 20 minutes at 300×g. After centrifugation five layers could be identified in the centrifuge tube. The lowest layer contained motile sperm and the next layer up contained immotile sperm. Each layer was carefully transferred to new conical centrifuge tubes without disturbing the other layers. Using a transfer pipette, 2-3 mL of PureSperm wash was added to tubes containing either motile sperm or immotile sperm, and the re-suspended pellet was centrifuged for 15 minutes at 500×g. After purification, the motility was ≥95% in the motile fraction and <10% in the immotile fraction.

Real-Time Quantitative RT-PCR

Total RNA was isolated using the RNAeasy mini kit (Qiagen, Valencia, Calif., USA) with on-column DNase digestion using an RNase-free DNase set (Qiagen, Valencia, Calif., USA) according to the manufacturer's instructions. RT-PCR was also performed by the TaqMan gene expression assay (Applied Biosystem) using an Applied Biosystems 7500 Fast Real-Time PCR System. Primers and probes [β-actin: Hs01060665_g1, Atp6v0a2: Hs00429389_m1] for TaqMan assays were obtained from Applied Biosystems. The procedure was as follows: 1.0 μg total RNA was used to synthesize cDNA by reverse transcription using the First Strand cDNA (Roche Applied Science, Indianapolis, Ind., USA) in a 20-μl volume. PCR amplification was performed in a total volume of 20 μl, containing 5 ng of the cDNA derived from reverse transcription, 25 pmol of each primer, and 10 μl iQ Taqman mastermix. Each reaction was incubated for 2 min at 50° C., 10 min at 95° C., and then subjected to 60 cycles involving denaturation at 95° C. for 15 s and annealing/extension at 60° C. for 1 min. The threshold cycle (TC) for fluorescence development was measured. All samples were run in triplicate. The ratios of the transcript levels of genes of interest in experimental and control samples were compared with the ratios of β-actin transcript levels in corresponding samples since β-actin is widely considered a stable reference in this methodology.

ELISA for a2NTD

The levels of N-terminal portion from Atp6v0a2 (a2NTD) were measured using sandwich enzyme-linked immunosorbent assay (ELISA). First, chicken anti-a2NTD was added to polystyrene trays over night. After discarding this antibody, 100 μl of sperm free seminal fluid samples were added to each well filled with 25 μl of incubation buffer and then incubated with 50 μl of biotinylated chicken anti-a2NTD at room temperature for 2 h. After the wells were aspirated and washed four times, 100 μl of streptavidin-HRP working solution was added to each well and incubated at room temperature for 30 min. Then the wells were washed four times and incubated with 100 μl of stabilized chromogen solution (R&D system) at RT for 30 min in the dark. The reaction was stopped with 100 μl of stop solution, and then the absorbance was read at 450 nm.

Western Blotting

Washed sperm was placed in SDS sample buffer and boiled for 5 minutes. Equal amounts of sperm lysates were resolved on 4-20% SDS-PAGE followed by transfer onto a nitrocellulose membrane. The blots were then probed with chicken anti-Atp6v0a2 polyclonal antibody (3 ug/ml) (anti-a2V) or mouse anti human β-actin (Sigma-Aldrich, St Louis, Mo., USA) followed by donkey anti-chicken IRDye-800CW (1:20,000), and goat anti-mouse IRdye-680CW (LI-COR Biosciences, Lincoln, Nebr., USA) respectively. Fluorescent blots were imaged on the Odyssey Infrared Imaging System (LI-COR Biosciences, Lincoln, Nebr., USA).

Immunofluorescence Staining

Motile and immotile sperms were isolated as described above and then fixed in 4% paraformaldehyde overnight at 4° C., and then air-dried onto slides. Spermatozoa were permeabilized with 0.1% Triton X-100 in PBS for 10 min at room temperature, then washed with PBS. Slides were then incubated with primary chicken anti-Atp6v0a2 polyclonal antibody (1:50), diluted in 1% BSA overnight at 4° C. Slides were washed with PBS three times for 10 min each, then incubated with donkey anti-chicken IgG secondary antibody conjugated with FITC (1:40, 0.5 h, at 37° C.), then washed and mounted in Vectashield with DAPI (Vector Laboratories, Burlingame, Calif.) and stored at 4° C. in the dark. The stained slides were viewed under a fluorescent microscope (Nikon Eclipse 80i; Nikon Inc, Tokyo, Japan). The fluorescence of FITC was monitored using a B-2 filter with a 495 nm band pass barrier filter.

Multiplex Assays

All procedures were following manufacturer's instructions (Milliplex MAP kit, Millipore). A volume of 25 μl of undiluted semen was used for measuring chemokines and cytokines A volume of 25 μl of magnetic beads (bead size=6.45μ coated with specific antibodies (RCYTOMAG-80K-PMX, Milliplex MAP Kit, Millipore) was added to the sample and the reaction was incubated at 4° C. for 24 h. The beads were washed and incubated with 25 μl of biotinylated detection antibody at room temperature for 2 h. To complete the reaction 25 μl of Streptavidin-Phycoerythrin conjugate compound was added and allowed to incubate for 30 min at room temperature. The beads were then washed and incubated with 150 μl of sheath fluid for 5 min at room temperature.

The samples were analyzed on the MAGPIX instrument. The concentration of the analytes was then determined using the Bio-Plex Manager version 5.0 and MAGPIX xPONENT software, respectively. The assays were run in triplicate to confirm the results. Analytes were normalized to total protein concentration which was estimated with a Bradford assay, a colorimetric protein assay. Eleven analytes were determined: IL-1β, IL-2, IL-4, IL-6, IL-10, IL-12p70, IFN-γ, chemokine C—C motif ligand 2 (CCL2, previously known as monocyte chemoattractant protein 1, MCP-1), chemokine C—C motif ligand 3 (CCL3, previously known as macrophage inflammatory protein 1 alpha, MIP-1α), TNF-α, granulocyte colony-stimulating factor (G-CSF), and granulocyte-macrophage colony-stimulating factor (GM-CSF).

Statistical Analysis

A detailed statistical analysis was performed using SPSS version 20. Mann-Whitney U-test was applied to compare Atp6v0a2 mRNA and protein levels, and student t-test for the comparison of sperm parameters, seminal fluid cytokine and chemokine levels of the two groups. Spearman's test was used to determine correlations between a2NTD and cytokine and chemokine levels. A probability of <0.05 was considered to be significantly different.

Results

Characteristics of Study Population

The semen profiles of infertile men (study group) and normal sperm donors (controls) are shown in Table 1. Semen from controls had no abnormal parameters. On the other hand, semen from study group had at least one or more abnormal findings in sperm volume, concentration, motility or morphology. Semen volume (P≤0.01), sperm concentration (P≤0.05) and sperm motility (P≤0.01) of study group were significantly decreased in the infertile men when compared to the normal fertile donors.

Atp6v0a2 mRNA and Protein Expression in Human Sperm

Figure 1B:
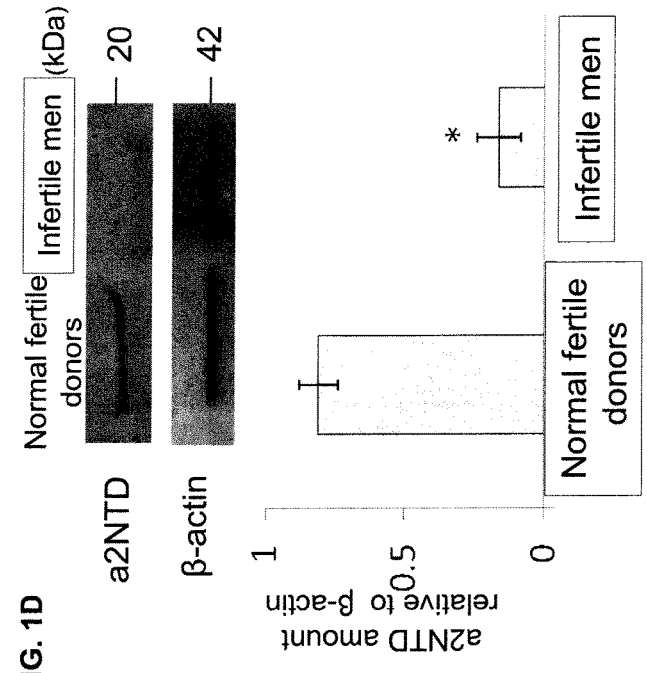

The Atp6v0a2 gene expression was analyzed by real time PCR in the spermatozoa recovered from infertile men and normal fertile donors (n=18 each). The level of Atp6v0a mRNA was significantly decreased in the spermatozoa recovered from infertile men when compared to the normal fertile donors (P≤0.05) (FIG. 1A). Western blotting analysis was confirmed that Atp6v0a2 protein was significantly lower (P≤0.05, n=5) in the spermatozoa recovered from infertile men when compared to the normal fertile donors (FIG. 1B).

Levels of Secreted a2NTD in Seminal Fluid

Figure 1C:
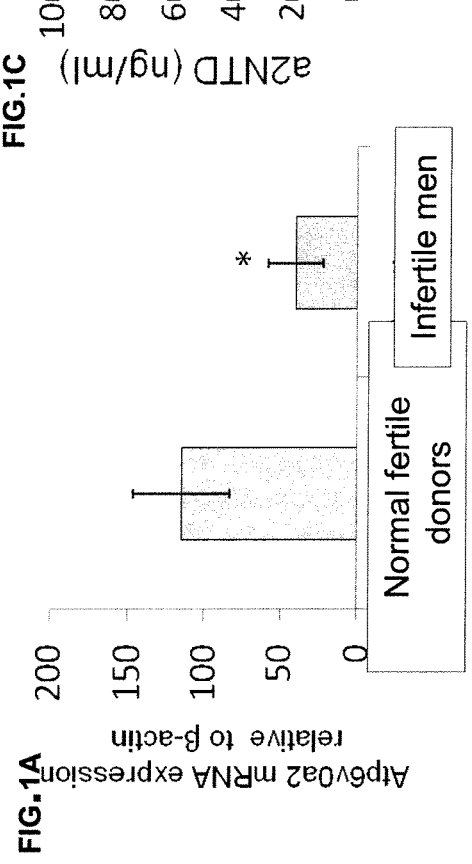
Figure 1D:
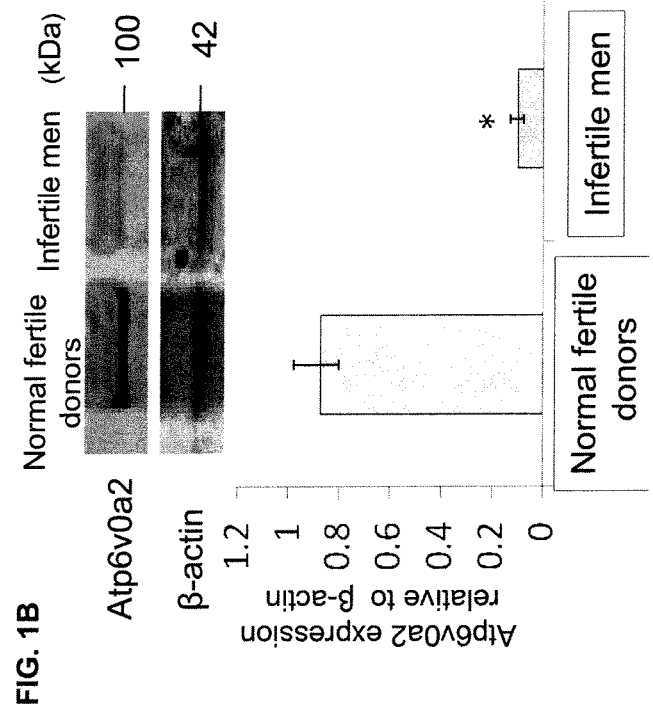

The concentration of secreted a2NTD was measured in the spermatozoa-free seminal fluid recovered from infertile men and normal fertile donors. Secreted a2NTD protein was significantly higher in normal fertile donors group (57.9±11.0 ng/ml, n=20) when compared to infertile men group (45.7±16.3 ng/ml, n=20; P≤0.01) (FIG. 1C). Similarly, western blot analysis of semen with anti-a2NTD shows that a2NTD was detected in ~20 kDa band, and its level was significantly higher in normal fertile donors group compared to infertile men group (P≤0.05, n=6 each) (FIG. 1D).

Seminal Fluid Cytokine and Chemokine Profiles

The concentrations of MCP-1 (P≤0.05), GM-CSF (P≤0.01), G-CSF (P≤0.01), and MIP-1α (P≤0.01) was significantly decreased in the spermatozoa-free seminal fluid recovered from infertile men group when compared to the normal fertile donors group. In contrast, there were no significant differences in IFN-γ and IL-12 between spermatozoa-free seminal fluid from both studied groups (FIG. 2). TNF-α, IL-1β, IL-2, IL-4, IL-6 and IL-10 could not be detected in seminal fluid since they were below the sensitivity level of the assay and presumably very low. Previously we have shown a2NTD induces the secretion of various chemokine and cytokines in the female reproductive tract. To study whether secreted a2NTD of seminal fluid is associated with secretion of various cytokines and chemokines, linear correlation was performed. Significantly positive correlations were observed between the level of a2NTD and G-CSF (P≤0.01), GM-CSF (P≤0.01), MCP-1 (P≤0.05) and MIP-1α (P≤0.01) in seminal fluid.

Figure 3C:
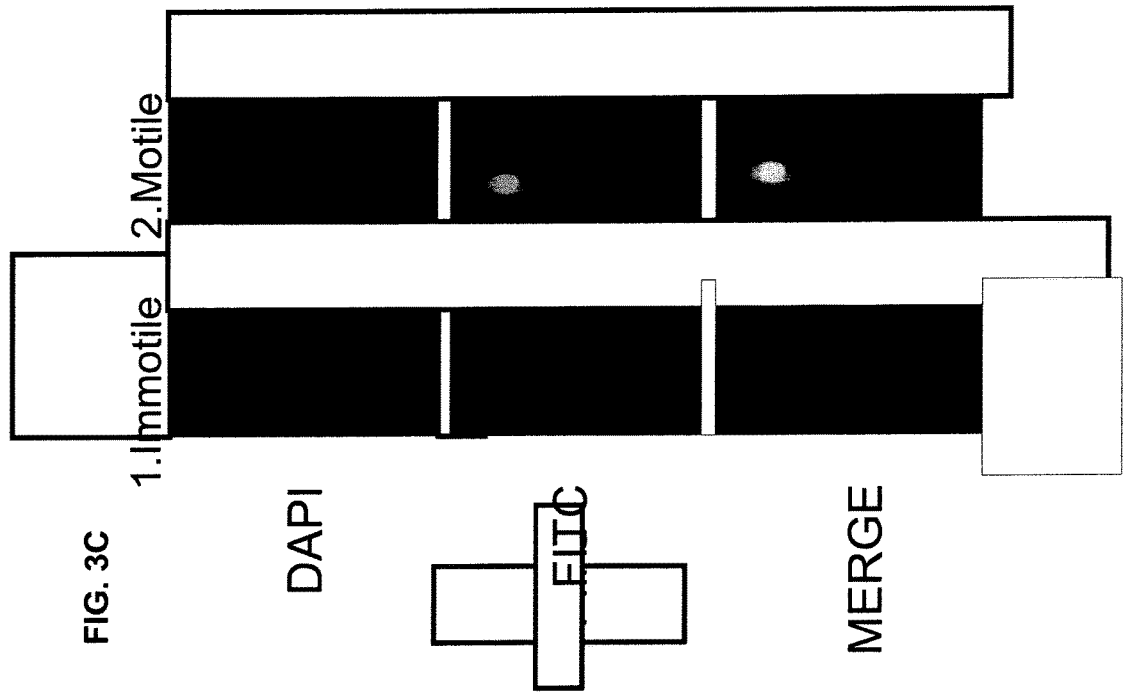
FIGS. 3A-3C: The expression of Atp6v0a2 protein in motile and immotile spermatozoa by Western blots and fluorescent microscopy.
Figure 3A:
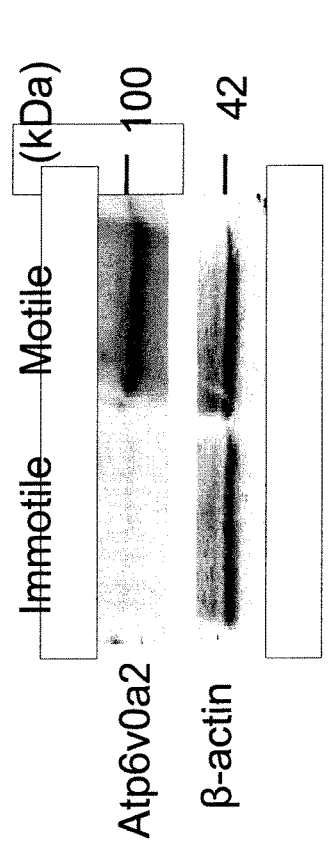
Figure 3B:
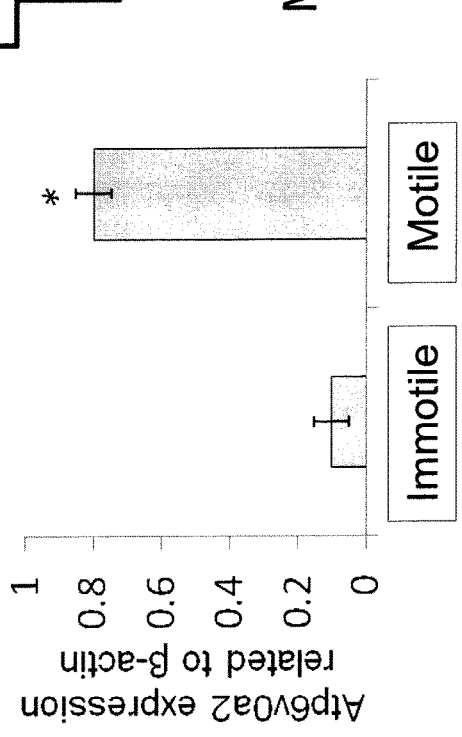

The Expression Levels and Immunolocalization of Atp6v0a2 Protein in Immotile and Motile Sperm Collected from Normal Sperm To determine the association of Atp6v0a2 protein with the sperm motility, Atp6v0a2 protein level was checked in the motile and immotile spermatozoa. Western blot analysis shows that the expression of Atp6v0a2 protein was significantly (P≤0.01; n=6 each) higher in motile spermatozoa compared to immotile spermatozoa from normal fertile donors (FIG. 3A-B). (FIG. 3B). These results suggest that the increased Atp6v0a2 protein was associated with motility of human spermatozoa.

Immunohistochemistry analysis was performed to examine the expression and localization of Atp6v0a2 protein in motile and immotile spermatozoa from normal controls. Atp6v0a2 protein was not detected in immotile spermatozoa (FIG. 3C; panel 1) however, in motile spermatozoa Atp6v0a2 protein was abundantly detected and localized in the acrosomal region (FIG. 3C; panel 2).

Discussion

Sperm delivers not only the male genome to the ova but several crucial molecules such as mRNA and proteins which are required for fertilization and early embryonic development. Our previous studies suggested a possibility that Atp6v0a2 in sperm may have an important role in fertilization. In this study, we demonstrate that Atp6v0a2 is highly expressed in normal human sperm but only weakly expressed in sperm from infertile men. Additionally, Atp6v0a2 was highly expressed in motile sperm but not immotile sperm when normal sperm were used. These findings suggest that Atp6v0a2 in sperm plays an important role in the fertilizing capacity of human sperm as well as it does in murine sperm.

The acrosomal region is known to be an acidic secretory vesicle containing hydrolytic enzymes that are involved in the passage of the sperm across the zona pellucida. Thus, the assembly of a proton pump is an essential step for the biogenesis of this unique organelle. Previously, we demonstrated that Atp6v0a2 was localized in the acrosomal region of capacitated sperm in murine. The intracellular pH of sperm is a key factor that controls mature mammalian sperm stored in the caudal part of the epididymis and the vas deferens. Sperm are essentially quiescent and are kept immotile primarily by an acidic intracellular and extracellular pH. Seminal fluid is more alkaline (pH>7.0) and provides a suitable environment for alkalization of the sperm cytoplasm and activation of sperm motility. Recently, it was shown that V-ATPases at the plasma membrane regulate the pH of intracellular organelles which activate sperm motility and is solely responsible for the acrosomal-region-acidification.

It is possible that Atp6v0a2 could play a role in spermatogenesis as pH-sensor. The present results clearly indicated that Atp6v0a2 is more abundantly expressed in motile sperm than in viable immotile sperm. In accordance with studies of capacitated sperm in the murine model, Atp6v0a2 was predominantly localized in the acrosomal region in human normal sperm. Atp6v0a2 is likely to be involved in differentiation of motile sperm as a pH modulator. Furthermore, we reported that Atp6v0a2 plays a role in the successful implantation of a murine embryo. We found that the expression of Atp6v0a2 is remarkably greater in the egg fertilized by capacitated sperm than in the egg fertilized by non-capacitated sperm. Therefore, Atp6v0a2 in human sperm may be a vital molecule not only controlling intracellular pH, but also contributing to embryogenesis.

The role of maternal immune responses in the developing embryo has been intensely studied. It is known that various mechanisms exist to prevent a potentially deleterious maternal immune response, which, would result in compromising the survival of the semi-allogeneic fetus. However, it is also known that several inflammatory cytokines, which are potentially harmful to the fetus, are necessary for successful implantation during the preimplantation period. Thus, close immune cooperation is required during the course of a successful pregnancy. There is an early inflammatory stage followed by an anti-inflammatory stage and both are required to for a successful pregnancy. Previously, we reported that capacitated sperm initiates inflammation in the maternal side by the release of the immune regulatory molecule a2NTD, which in turn induces the expression of inflammatory cytokines such as LIF, IL-1β, and TNF-α. In other studies, we showed that the key portion of the a2V protein, a2NTD (the N-terminal portion) is released from the activated monocyte and induces the cytokine secretion. In this study, we showed that seminal fluid from normal sperm donor was enriched with secreted a2NTD and the level of a2NTD was significantly correlated with the levels of G-CSF, GM-CSF, MCP-1 and MIP-1α. The strongest correlation was found between a2NTD and G-CSF in seminal fluid (positive correlation coefficient of 0.784). Elevated seminal fluid concentrations of cytokines and chemokines have been associated with poor semen quality and male infertility. Furthermore, there is increasing evidence that many of these cytokines can adversely affect spermatogenesis. Therefore, these findings suggest that a2NTD in seminal fluid is likely to contribute to the establishment of a biphasic immunological milieu for spermatogenesis and implantation.

Chemokines are a family of more than 30 chemo-attractant cytokines involved in leukocyte migration, angiogenesis and cell activation. They play important roles in events associated with inflammation and immune defense, and probably have similar roles in the male reproductive tract. MCP-1, which recruits monocytes, memory T cells, and dendritic cells to sites of tissue injury, infection, and inflammation, can control Th2 polarization to maintain the maternal immune tolerance toward the allogeneic fetus. Previously, we have reported that MCP-1 can induces expression of uterine Atp6v0a2 in animal model. In this study, we demonstrated that MCP-1 in seminal fluid from normal sperm donor was significantly increased compared to seminal fluid from infertile men as well as a2NTD. Thus, it is possible that MCP-1 and a2NTD have a synergetic effect to establish immunological milieu at the implantation site, though further research is necessary to determine their roles in maternal-fetal tolerance.

Seminal fluid elicits expression of pro-inflammatory cytokines and chemokines, and a robust recruitment of macrophages, dendritic cells, and memory T cells. The leukocyte and cytokine environment induced in the cervix by seminal fluid appears competent to initiate adaptations in the female immune response that promote fertility. In this study, MIP-1α was present at comparatively high concentrations in seminal fluid from infertile men and normal sperm donor. However, MIP-1α in seminal fluid from normal sperm donor is more abundant than in sperm from infertile men. Increased expression of MIP-1α occurs during peri-implantation window in endometrium. In addition, MIP-1α in seminal fluid initiates a surge in the synthesis of other cytokines e.g., IL-6, which subsequently elicits the recruitment and activation of antigen-presenting cells into the endometrial stroma where they engulf and process paternal ejaculate antigens.

Seminal fluid from normal sperm donor was characterized by higher levels of G-CSF compared with seminal fluid from infertile men suggesting that it also may have a role, as yet undefined. G-CSF, which participates in subsequent placental granulocytosis, can modulate the production of deleterious levels of IFN-γ (which we report to be comparatively low in both seminal fluid from infertile men and normal sperm donor), which is known to impair human trophoblast cell growth and function in vitro and to cause abortion in murine model. G-CSF delays apoptosis in neutrophils by activating the V-ATPase. These data may help to explain the mechanism by which the seminal fluid from sperm which express Atp6v0a2 has sufficient amounts of MIP-1α and G-CSF to enable the induction and maintenance of the maternal immune tolerance toward the allogeneic fetus. Robertson et at reported that a cytokine network in seminal fluid is required in fertilization, and GM-CSF is a key factor regulating fertility that targets both reproductive tract dendritic cells and the developing embryo. In this study, we also showed that GM-CSF could be detected although levels of GM-CSF were not significantly different between seminal fluid from normal sperm donor and seminal fluid from infertile men. The discrepancies in this report may be partly because of different assay techniques or study populations.

Over the past decade a number of laboratory tests have been developed to determine properties of sperm function but few have been adopted into routine clinical use in place of the WHO semen analysis. Therefore, we should understand the limitations of this definition since dysfunctional sperm can exist in spite of normal standard parameters. In this study, we analyzed whether Atp6v0a2 is associated with sperm status diagnosed with the WHO semen analysis and showed that lower Atp6v0a2 expression in sperm from infertile men was consistent with "abnormal" based on WHO semen analysis (i.e., parameters were lower than the standards indicated for semen volume, number and motility and morphology). With regard to sperm motility, we found that Atp6v0a2 in motile sperm was expressed at higher levels than in immotile sperm. This result strongly suggested that Atp6v0a2 is potentially useful for the evaluation of sperm motility whether semen is diagnosed normal or abnormal based on WHO semen analysis standards.

In summary, Atp6v0a2 protein and mRNA in sperm from infertile men was significantly lower compared to that of normal sperm. Fluorescent microscopy revealed that higher expression of Atp6v0a2 mRNA and protein in the acrosomal region motile sperm than immotile sperm. Secreted a2NTD in seminal fluid from normal sperm donor was significantly higher than infertile men. Furthermore, a2NTD expression correlated with levels of cytokines and chemokines which are required for fertilization and spermatogenesis. In conclusion, a critical level of Atp6v0a2 may be necessary for the normal function of sperm. The absence or decreased level of Atp6v0a2 may predict male infertility.

TABLE 1

Characteristics of the semen samples from infertile men and normal fertile donors (n = 35 each).

| | Infertile men | Normal fertile donors |
|---|---|---|
| Semen volume (ml) | 1.5 ± 0.1 | 3.2 ± 0.3** |
| Spermatozoa concentration (×10 * 6/ml) | 62.4 ± 35.8 | 80.0 ± 28.8* |
| Motility (%) | 24.0 ± 16.1 | 60.2 ± 13.7** |

Note:
data presented as means ± standard deviation
*$P < 0.05$;
**$P < 0.01$ with respect to normal fertile donors Kits for Determining Fertility of a Seminal Sample The present invention further provides a kit for preparing a seminal sample for determining male fertility of the sample by any suitable enzyme-based assay such as ELISA, or, even more preferably, in a multiplex assay. The kit will include a supply of enzyme-linked antibodies particular for the analytes Atp6v0a2, G-CSF, MIP 1α, and MCP-1. The kit will also include a substrate for binding the enzyme-linked antibody and can include beads, microspheres, a microtiter plate, or all. The words "beads" and "microspheres" will be used interchangeably. The components of the kit are contained in suitable packaging for shipping and handling and include a set of instructions for using the kit to determine the fertility of a seminal sample.

In one preferred form of the invention, each enzyme-linked antibody is bound to a unique substrate and more preferably to a unique microsphere. Suitable microspheres have a unique characteristic to distinguish one batch of microspheres from other batches. In one preferred form of the invention, the unique characteristic will be the size of the microsphere, the shape of the microsphere, a color of the microsphere, or an electromagnetic spectrum of the microsphere. Suitable microspheres can be fabricated from metal, plastic, and combinations of the same. Preferred metals include those that are responsive to a magnetic field and include metals, metal-containing minerals, or metal-containing composite materials. Materials that are responsive to a magnetic field will have magnetic properties such as ferromagnetism, ferrimagnetism, paramagnetism, and superparamagnetism. In one preferred form of the invention, the material is iron. Suitable metal-containing minerals include, most preferably, magnetite. In another preferred form of the invention, the microspheres will have magnetic properties but with little or negligible magnetic remanence.

Preferred plastics include polystyrene, polyolefins, polyamides, polyimides, polysulfones, polyesters, proteins and other biological materials. In another preferred form of the invention, the plastic is rendered magnetic by the presence of one of the metals, metal-containing minerals, or metal-containing composite materials set forth above and most preferably the microsphere will include an effective amount of magnetite. The magnetic material can be added to the plastic and incorporated in a homogeneous fashion throughout the microsphere when the plastic is in a molten state, can be coated on an outside surface of the microsphere, or can be incorporated by other means into the plastic material.

In one preferred form of the invention, each batch of beads will have a unique color defined by a combination of two different dyes and even more preferably the combination of varying quantities of a red dye and an infrared dye. In one preferred form of the invention, the beads will have a diameter from about 400 nm to about 10 μM, more preferably from about 4 μM to about 7 μM. Preferably the microspheres are suspended in a liquid such as water and at a concentration from about 500,000 beads per milliliter to about 15 million beads per milliliter. Suitable beads are sold by LUMINEX® Corporation under the trademarks MAGPLEX® and MICROPLEX®.

The antigen recognized by the antibody for Atp6v0a2 has a sequence of YSSSHPPAEHKKMVLWNDSVVRH (SEQ. ID NO. 1). The antibody for G-CSF, MIP 1α, and MCP-1 are obtained from Milliplex Map kit (Millipore) under the designation MCTYOMAG-70K. Each antibody is exposed to a unique batch of beads, incubated, and washed. The four different batches of coated beads are placed within a container system from one container to four containers to define the first container system and most preferably the four batches of beads are combined into a single container.

Suitable antibodies will have a functional group that can be detected by suitable scientific instrumentation or is capable of reacting with another molecule or agent to cause a change in color, fluorescence, electromagnetic spectral signature to allow for quantitation of the analytes of interest. In one form of the invention, the enzyme-linked antibodies will have a biotin group or be biotinylated.

In one preferred form of the invention, the agent will be contained within a second container system and is a streptavidin-containing compound, and more preferably a monovalent streptavidin and even more preferably, streptavidin bound to a chromophore. In one preferred form of the invention, the chromophore is phycoerythrin. When the biotinylated antibody is exposed to streptavidin-R-phycoerythrin, the amount of the analyte can be determined by exposing the beads to an excitation source having a wavelength of 488 nm.

The kit will also include a set of instructions for using the components of the kit with a seminal sample to determine the fertility of the sample. An end user of the kit will obtain a seminal sample from a human patient, the seminal sample will be combined with the contents of the first container system for an effective period of time for the analytes to bind to the enzyme-linked antibodies to form a test sample. Then the agent from the second container system will be combined with the test sample and incubated for an effective period of time such as about 30 minutes. The test sample will be washed with phosphate buffered saline and will be frozen to a temperature below minus 5° C. and sent to a testing facility.

The kit will also optionally include a third container system of a capacitation buffer. The capacitation buffer is, in a preferred form of the invention, a Krebs-Ringer buffer and is supplemented with BSA, $HCO_3^-$, and $Ca^{++}$. The capacitation buffer will be added in equal volume to the seminal sample and allowed to sit for 30 minutes.

The kit can also optionally contain a plate having a plurality of spaced wells for receiving one of each of the enzyme-linked antibodies, a suitable amount of sample, a detection agent and a control. In a preferred form of the invention, the plate is a microtiter-type plate made from plastic, preferably polystyrene, and has 96 wells in an array of 8 wells by 12 wells.

Method for Testing Samples in a Multiplex Array

A designated testing facility will receive the frozen sample and thaw it to prepare for analysis. The thawed sample will be mixed by stirring or shaking and suitable quantities will be added to the wells of a microtiter plate and subjected to analysis by a MAGPIX instrument sold by the LUMINEX® Corporation. The quantities of the analytes will be determined and compared to recombinate peptide standards containing the molar concentrations of the peptide antigen to be determined. The test samples will be compared to known standards. A fertile sample is confirmed if the quantities of one of the four analytes, more preferably two of the analytes, more preferably three of the analytes, and most preferably the quantities of all four of the analytes in the test sample will exceed those in the control sample. The test results will then be reported to the appropriate entity or person.

A Method for Preparing a Seminal Sample for an Artificial Insemination Procedure:

The present invention further provides a method for preparing a seminal sample for an artificial insemination procedure ("AI") to increase fertilization outcomes. The method includes obtaining a seminal sample, adding to the sample an effective amount of a capacitation buffer; and adding to the sample an effective amount of a protein cocktail of one or more of the proteins selected from the group consisting of a2NTD, G-CSF, GM-CSF, MIP 1α, and MCP-1 to enhance the fertility potential of a seminal sample. The protein cocktail comprises from 0.5 cc to 1.0 cc a2NTD, from 0.5 cc to 1.0 cc G-CSF, from 0.5 cc to 1.0 cc GM-CSF, from 0.5 cc to 1.0 cc MIP 1α, and from 0.5 cc to 1.0 cc MCP-1.

Unlike prior art AI procedures where a substantially reduced number of sperm cells are used in the procedure, the present method uses essentially all of the sperm cells from the initial sample. That is to say, there is no effort to reduce the number of sperms cells from the sample.

The method further includes exposing the enhanced seminal plasma and sperm sample to an egg to fertilize the egg. Seminal plasma and sperm will be exposed to the capacitation buffer containing a2NTD for 5 to 20 minutes. The capacitated sperm will have greater potential to fertilize an egg that has been obtained by AI than non-capacitated sperm and will result in more successful fertilized eggs for AI procedures.

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

I claim:

1. A kit for determining male fertility comprising:
    a first container system consisting essentially of four different batches of antibodies each linked to a functional group one of each of the four batches of antibodies capable of binding selectively to one of each of the analytes Atp6v0a2, G-CSF, MIP 1α, and MCP-1;
    packaging for holding the first container system; and
    instructions for using the four batches of antibodies with a seminal sample to determine the fertility of the sample.

2. The kit of claim 1 further comprising in the first container system four batches of microspheres, each batch of the four batches of microspheres having a unique characteristic that distinguishes one batch from all of the other batches, one of each of the four batches of antibodies being exclusively bound to one of each of the four batches of microspheres.

3. The kit of claim 2 wherein the unique characteristic is a size, shape, color, or electromagnetic spectrum.

4. The kit of claim 2 wherein the microspheres are made from plastic or metal.

5. The kit of claim 2 wherein the microspheres are magnetic.

6. The kit of claim 3 wherein each color is defined by a ratio of the amount of a first dye and an amount of a second dye.

7. The kit of claim 1 further comprising a second container system containing a capacitation buffer.

8. The kit of claim 7 wherein the capacitation buffer comprises Krebs Ringer Buffer.

9. The kit of claim 1 further comprising a container of isotonic saline.

10. The kit of claim 1 further comprising a plate having a plurality of spaced wells for receiving one of each of the four batches of antibodies and a control.

11. The kit of claim 1 further comprising a third container system of streptavidin bound to a chromophore.

12. The kit of claim 11 wherein the streptavidin is monovalent.

13. The kit of claim 11 wherein the chromophore is phycoerythrin.

14. The kit of claim 1 wherein the antigen recognized by the antibody for Atp6v0a2 comprises SEQ. ID NO. 1.

* * * * *

SEQUENCE LISTING

<160> NUMBER OF SEQ ID NOS: 1

<210> SEQ ID NO 1
<211> LENGTH: 23
<212> TYPE: PRT
<213> ORGANISM: Homo sapiens

<400> SEQUENCE: 1

-continued

```
Tyr Ser Ser Ser His Pro Pro Ala Glu His Lys Lys Met Val Leu Trp
1               5                   10                  15

Asn Asp Ser Val Val Arg His
            20
```